United States Patent [19]

Los

[11] 4,062,671

[45] Dec. 13, 1977

[54] IMIDAZOISOINDOLEDIONES, AND THE USE THEREOF AS HERBICIDAL AGENTS

[75] Inventor: Marinus Los, Pennington, N.J.

[73] Assignee: American Cyanamid Company, Stamford, Conn.

[21] Appl. No.: 733,635

[22] Filed: Oct. 18, 1976

Related U.S. Application Data

[62] Division of Ser. No. 631,357, Nov. 12, 1975, Pat. No. 4,017,510.

[51] Int. Cl.$^2$ ............................................. A01N 9/22
[52] U.S. Cl. ...................................................... 71/92
[58] Field of Search ............................................. 71/92

[56] References Cited

U.S. PATENT DOCUMENTS

| | | | |
|---|---|---|---|
| 3,409,425 | 11/1968 | Bousquet | 71/76 |
| 3,849,436 | 11/1974 | Johnson | 71/92 X |

*Primary Examiner*—Lewis Gotts
*Assistant Examiner*—Catherine L. Mills
*Attorney, Agent, or Firm*—H. G. Jackson

[57] ABSTRACT

The invention relates to novel imidazoisoindoledione compounds including the optical isomers thereof. This invention also relates to a method for the control of undesirable plant species with the imidazoisoindolediones and their optical isomers, and further, to a process for the preparation of the compounds.

11 Claims, No Drawings

IMIDAZOISOINDOLEDIONES, AND THE USE THEREOF AS HERBICIDAL AGENTS

This is a division of application Ser. No. 631,357 filed Nov. 12, 1975 now U.S. Pat. No. 4,017,510.

BACKGROUND OF THE INVENTION

1. Field of the Invention

The invention pertains to new organic chemicals and their herbicidal use.

2. Description of the Prior Art

Intermediates useful in the manufacture of the compounds of the invention are disclosed in Netherland Pat. No. 7,311,503, published February 25, 1974 and assigned to the American Cyanamid Company. The corresponding U.S. application is copending Ser. No. 382,418 filed July 25, 1973 now U.S. Pat. No. 3,940,419.

SUMMARY OF THE INVENTION

The invention relates to compounds having a structure represented by a formula:

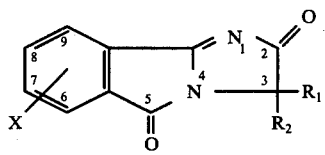

wherein X is H, $CH_3$, $NO_2$, Cl, $OCH_3$ or $SCH_3$; $R_1$ is alkyl $C_1$–$C_4$; $R_2$ is alkyl $C_1$–$C_6$, cycloalkyl $C_3$–$C_6$, alkenyl $C_2$–$C_4$, phenyl, halophenyl or benzyl; and when $R_1$ and $R_2$ are taken together with the carbon to which they are attached may form cycloalkyl $C_3$–$C_6$ optionally substituted with methyl; and the optical isomers thereof. Numbering of the imidazoisoindoledione ring system is shown in formula I above. The invention further relates to a method for controlling undesirable plant species with the above-identified compounds. It also relates to a method for regulating the growth of plants, and further, to methods for the preparation of the compounds, including methods for the preparation of the isomers thereof.

DESCRIPTION OF THE PREFERRED EMBODIMENTS

Preferred compounds for use as herbicidal agents are those represented by formula I above, wherein X, $R_1$ and $R_2$ are as described above, excepting that the sum of the carbon atoms represented by $R_1$ and $R_2$ is 2 to 4. Still more preferred compounds, which are useful as herbicidal agents, are formula I compounds wherein X is H, $CH_3$ or Cl; $R_1$ is alkyl $C_1$–$C_4$; $R_2$ is alkyl $C_1$–$C_3$ or cyclopropyl and the sum of the carbon atoms represented by $R_1$ and $R_2$ is $C_2$–$C_4$.

Preferred compounds for use as plant growth regulators claimed in Ashkar's copending application Ser. No. 631,359 filed Nov. 12, 1975 are represented by formula I above, wherein X, $R_1$ and $R_2$ are as described above, excepting that the sum of the carbon atoms represented by $R_1$ and $R_2$ is 4 to 7.

Advantageously, formula I imidazoisoindolediones can be prepared by several distinct synthesis routes, hereinafter described.

In accordance with this invention, formula I imidazoisoindolediones can be prepared by cyclization of a phthalimidocarboxamide or dioxoisoindolineacetamide. Cyclization can be achieved by reacting the phthalimido derivative or isoindolineacetamide with a strong base, at an elevated temperature in the presence of an organic solvent.

The cyclization reaction is preferably conducted at a temperature of from 80° C to 150° C. in the presence of a base such as sodium or potassium hydroxide, or a catalyst such as an aromatic sulfonic acid and a solvent which will form an azeotropic mixture with water, permitting virtually immediate removal thereof from the reaction mixture as it is formed.

Among the solvents which may be employed are toluene, benzene, xylenes and cyclohexane.

Bases which may be used include alkali metal hydroxides, alkali metal hydrides, alkali metal oxides, tertiary amines such as diisopropyl ethylamine, 1,5-diazobicyclo[3.4.0]-nonene-5; 1,5-diazobicyclo[5.4.0]undecene-5; 1,4-diazobicyclo[2.2.2]octane; tetramethylquanidine, potassium fluoride and quaternary ammonium hydroxides such as trimethylbenzyl ammonium hydroxide and strongly basic ion exchange resins.

Acidic reagents whch may be employed include aromatic sulfonic acids such as p-toluenesulfonic acid, β-naphthalenesulfonic acid, naphthalenedisulfonic acid, and the like.

In many cases, the ring closure may also be achieved by a simple pyrolysis of the phthalimidocarboxamide or dioxoisoindolineacetamide at a temperature between 80° C and 250° C.

This reaction may be illustrated as follows:

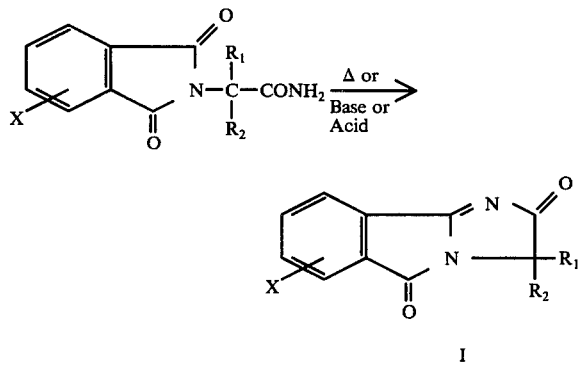

It should also be understood that, in the above reaction, when X is not hydrogen the product of the reaction is a mixture of the two isomeric compounds since cyclization occurs at either imide carbonyl group as illustrated below:

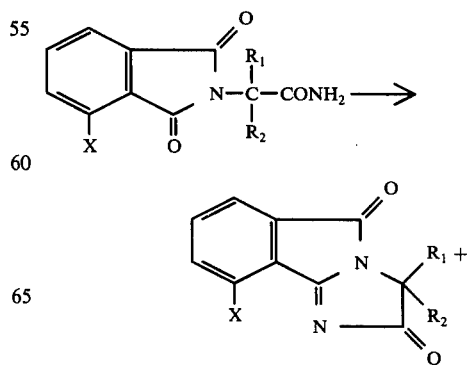

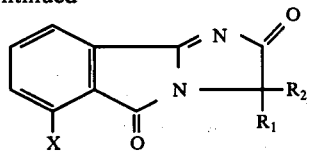

Furthermore, when $R_1$ and $R_2$ represent different groups, the carbon to which $R_1$ and $R_2$ are attached is an asymmetric center and the products (as well as their intermediates) exist in d- and l- forms as well as dl-forms. Formula I imidazoisoindolediones can also be prepared by cyclization of the appropriate N-(carbamoylalkyl) phthalamate with an alkali metal hydride such as sodium or potassium hydride, in the presence of an inert organic solvent such as toluene, xylene or benzene at an elevated temperature of about 80° C. to 150° C. This reaction may be illustrated using NaH as representative of the alkali metal hydride, as follows:

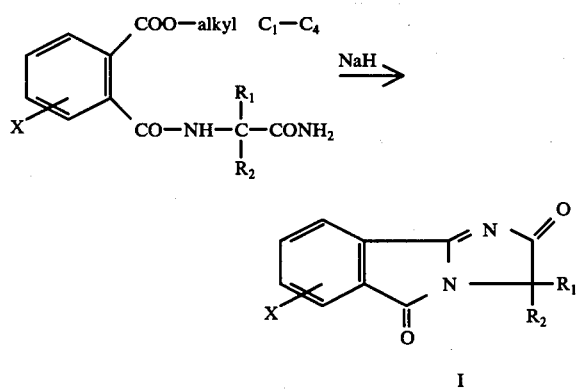

wherein X, $R_1$ and $R_2$ are as described above. This reaction is especially useful for the preparation of imidazoisoindolediones in which $R_1$ and $R_2$ represent bulky groups such as isopropyl or t-butyl groups.

Furthermore, as with the previously described method for the preparation of the formula I imidazoisoindolediones, when $R_1$ and $R_2$ represent different groups, the carbon atom to which they are attached is an asymmetric carbon atom. Therefore, if one starts with an optically active intermediate such as α-aminocarbonitrile, α-aminocarboxylic acid or α-aminocarboxamide, the intermediate N-(carbamoylalkyl) phthalamate and the imidazoisoindoledione, thus prepared, are optically active.

The intermediate phthalimidocarboxamide or dioxoisoindolineacetamide, which is essential to the preparation of the formula I imidazoisoindolediones of the present invention, can be prepared by first reacting an appropriate disubstituted ketone with ammonium chloride, sodium cyanide and ammonium hydroxide, to obtain the α,α-disubstituted-α-aminocarbonitrile. This α-aminocarbonitrile is then reacted with a phthalic anhydride to give the corresponding phthalamic acid.

This reaction is carried out at temperatures from about 20° C. to 60° C. in an inert solvent such as ether, tetrahydrofuran, chloroform, methylene chloride, benzene, toluene, and the like. The thus-formed phthalamic acid is then cyclized to the corresponding phthalimidocarbonitrile by heating with a dehydrating agent such as acetic anhydride, acetyl chloride, thionyl chloride, or the like, at temperatures from about 0° to 100° C. Hydration of the thus-formed phthalimidocarbonitrile is preferably carried out with a strong acid such as sulfuric acid, with or without the addition of a non-miscible solvent such as methylene chloride or chloroform and the like at temperatures from about −10° C to +30° C. These reactions are graphically illustrated by using the substituted phthalic anhydride as an example, and including the cyclization of the phthalimidocarboxamide to form the compounds of this invention, as follows:

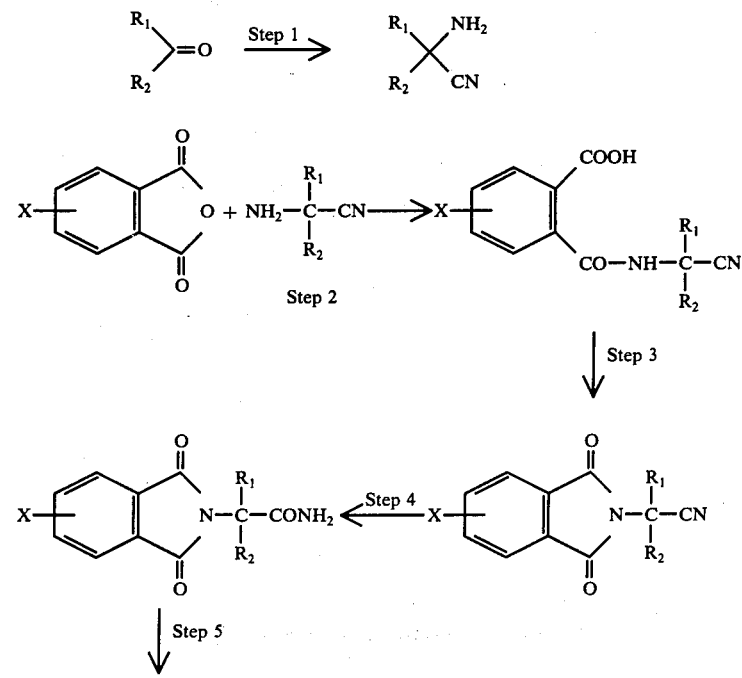

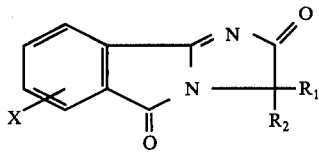

(I)

wherein X, $R_1$ and $R_2$ are as described above.

Alternatively, the above-mentioned intermediate phthalimidocarboxamide may also be prepared by the reaction of a phthalic anhydride with a substituted α-aminocarboxylic acid to obtain the phthalimidocarboxylic acid which is converted to the corresponding acid chloride using thionyl chloride. This reaction is generally conducted in the presence of an inert organic solvent such as toluene, benzene, or the like, at an elevated temperature. The acid chloride is then readily converted to the intermediate phthalimidocarboxamide by reaction with ammonia. This reaction is generally conducted in the presence of a solvent such as tetrahydrofuran at a temperature between about −10° C and +15° C. This synthetic route, including the cyclization of the phthalimidocarboxamide, is illustrated as follows:

N-(carbamoylalkyl) phthalamate with an alkali metal hydride. The N-(carbamoylalkyl) phthalamate, which is represented by the formula:

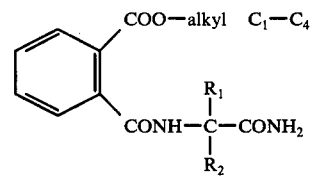

where $R_1$ and $R_2$ are as previously described, can be prepared by reacting an α-aminocarbonitrile with sulfuric acid at an elevated temperature to yield the corresponding α-aminocarboxamide. This carboxamide is then reacted with a 2-carboalkoxybenzoyl chloride to yield the N-(carbamoylalkyl) phthalamate, referred to above. These reactions may be graphically illustrated as follows:

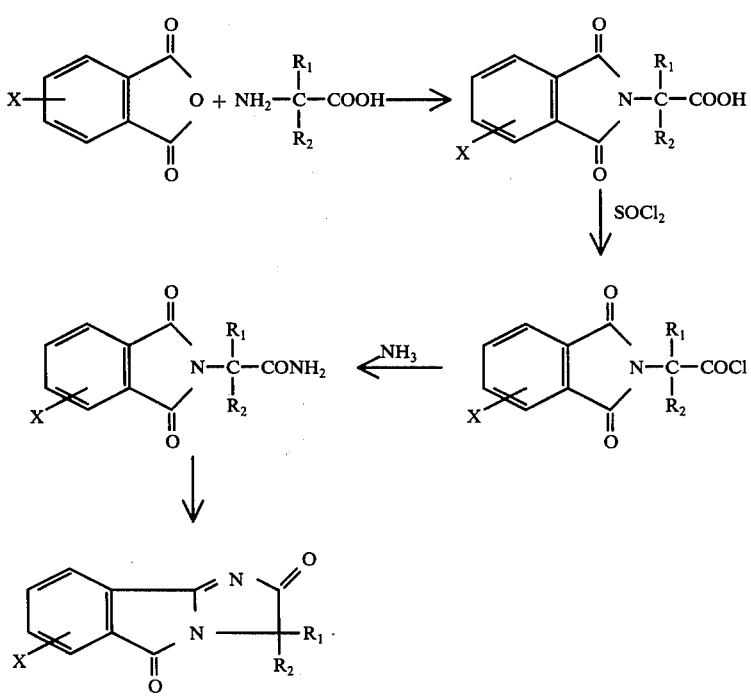

wherein X, $R_1$ and $R_2$ are as described above.

As previously indicated, formula I imidazoisoindolediones can also be prepared by cyclization of an

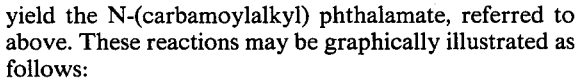

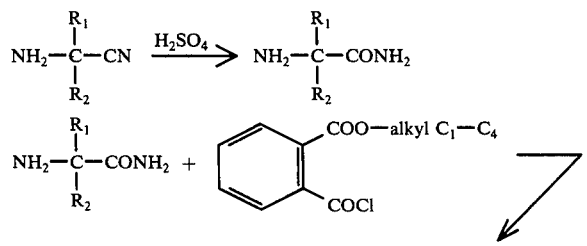

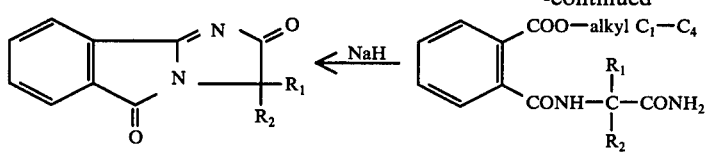

-continued

The compounds of the present invention are highly effective herbicidal agents. They may be used effectively for the control of both monocotyledonous and dicotyledonous plants by application thereof to the foliage of the plants, or by application to soil containing seeds on propagating organs of the plants. As such, said compounds are useful as preemergence and postemergence herbicides. Since they are only very slightly water soluble, they are generally formulated for foliar treatments as wettable powders, emulsifiable concentrates or flowable liquids which are usually dispersed in water or other inexpensive liquid diluent for application to the foliage as a liquid spray. However, when the compounds are to be used as preemergence herbicides where soil treatments are involved, the compounds of the invention may also be prepared as granular products.

A typical wettable powder can be prepared by grinding together approximately 46% by weight of a finely divided carrier such as attapulgite, 50% by weight of the imidazoisoindoledione of this invention, 3% by weight of the sodium salt of condensed naphthalene sulfonic acids and 1% by weight of sodium N-methyl-N-olcoyltaurate.

A typical flowable liquid can be prepared by admixing about 42% by weight of the imidazoisoindoledione, with about 3% by weight of the sodium salt of condensed naphthalene sulfonic acids, 2% by weight of finely divided bentonite and 53% by weight of water.

A granular product can be prepared by dissolving the imidazoisoindoledione in methylene chloride and spraying the thus-prepared solution on a granular carrier such as sand, silica, kaolin, corn cob grits, attapulgite, or the like.

In practice, I have found that the formula I compounds of the invention are effective postemergence herbicidal agents when applied to the foliage of undesirable broadleaf or grass plants, in an amount sufficient to provided from 0.07 to 11.2 kg/hectare, and preferably 0.3 to 4.5 kg/hectare of the active compound. I have also found that the compounds are useful for the preemergence control of undesirable broadleaf and grass plants when applied to soil containing seeds or propagating organo of the undesirable plants at a rate of between about 0.15 to 11.2 kg per hectare, and preferably 0.56 to 4.5 kg/hectare of active compound.

Also, in the method for controlling perennial species of undesirable plants about 18 to 27 kg/ha and preferably 18 to 22 kg/ha of active compound is required. I have also found that the compounds of the present invention are unique in their ability to control cyperaceous plants, particularly nutsedges, when applied to the soil in which the sedge nutlets and/or plants are present or growing. Among the Cyperaceae which can be controlled with the compounds of this invention are purple nutsedge (*Cyperus rotundus L.*), yellow nutsedge (*Cyperus esculentus L.*), false nutsedge (*Cyperus strigosus*) and the flatsedges, umbrella plants and kyllinga.

The compounds of this invention are likewise unique in their activity, especially preemergence herbicidal activity, toward perennial plants such as alligator weed, bindweed, milkweed, Canada thistle, Johnsongrass and quackgrass and woody perennials such as wild roses, blackberries, red raspberries and honeysuckle.

From the herbicidal evaluations exemplified below, it can be seen that the compounds of this invention are highly effective as preemergence herbicides for controlling woody plants, mustard, pigweed quackgrass, nutsedge, honeysuckle, wild rose and velvetleaf. As postemergence herbicidal agents, these compounds are especially effective for controlling mustard, pigweed, morningglory, barnyardgrass, crabgrass, green foxtail, wild oats and velvetleaf. As such, these compounds are particularly useful for clearing road sidings, railroad sidings, and areas beneath power lines.

In practice, I have further found that, at lower rates of application, the compounds of this invention exhibit plant growth regulating effects, especially dwarfing or growth-stimulating activity. Acitivity, of course, varies from chemical to chemical and plant to plant, but with pronounced plant growth regulating activity noted especially for compounds in which the sum of the carbon atoms represented by $R_1$ and $R_2$ is 2 to 7.

This invention is further demonstrated by the examples set forth below.

EXAMPLE 1

Preparation of 3-Isopropyl-3-methyl-5H-imidazo[2,1-a]-isoindole-2-(3H),5-dione.

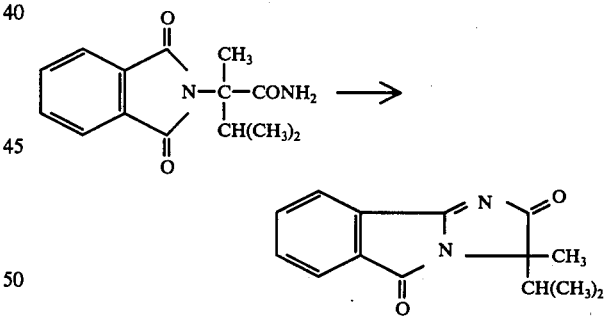

A solution of 130.1 g (0.5 mole) of α-isopropyl-α-methyl-1,3-dioxo-2-isoindolinearcetamide in 650 ml toluene is heated with vigorous stirring under a Dean-Stark water separator in order to remove traces of water. The solution was cooled to 100° C and 2.0 g sodium hydroxide in the form of pels is added and the mixture rapidly heated to reflux. Water collects in the water separator. One-half hour after the addition of the sodium hydroxide, a further 2 g is added and heating is continued for a further 1¼ hours when no further water is removed from the reaction mixture and the infrared spectrum of an aliquot indicates the reaction to be complete. The reaction mixture is cooled to room temperature, filtered and the solids washed with toluene and the toluene removed in vacuo to leave a white solid which is transferred to a filter funnel with hexane and air-dried to give 98.7 g of 3-isopropyl-3-methyl-3H-imidazo[2,1-a]isoindole-2,5-dione, melting point 93°–96° C. The product may be purified by recrystallization from hexane to give an analytically pure sample, melting point 98°–100.5° C.

Alternatively, the product may be isolated by adding a slight excess of glacial acetic acid over the amount of sodium hydroxide used to the toluene reaction mixture, adding water, separating the organic phase, washing the organic phase with water, separating the organic phase, drying the organic phase, and finally removing the solvent to yield the product.

The above procedure is repeated in all respects, excepting that the strong base reagent is altered. In separate experiments, sodium hydride, potassium hydroxide, barium oxide, diisopropylethylamine, 1,5-diazobicyclo]5.4.0]undicene-5, tetramethylguanidine, tetramethylbenzyl ammonium hydroxide, Amberlite A21 (Rohm & Haas) strongly basic ion exchange resin and p-toluenesulfonic acid, are substituted for sodium hydroxide and yield the desired 3-isopropyl-3-methyl-5H-imidazo[2,1-a]isoindole-2(3H),5-dione. In practice of the above-described method, sodium hydroxide or sodium hydride in refluxing toluene is preferred.

Using the procedure described above, but substituting the appropriate phthalimidocarboxamide or dioxoisoindolineacetamide for α-isopropyl-α-methyl-1,3-dioxo-2-isoindolineacetamide, and the selected strong base and solvent for sodium hydroxide and toluene, yields the imidazoisoindolinediones reported in Table I below. Table I also indicates the solvent and base used as well as the melting point of the compounds obtained. With regard to the compounds synthesized and reported in Table I, it should be understood that when $X \ne H$ the product is a mixture of two isomeric compounds, since cyclization occurs at both imidecarbonyl groups, for example:

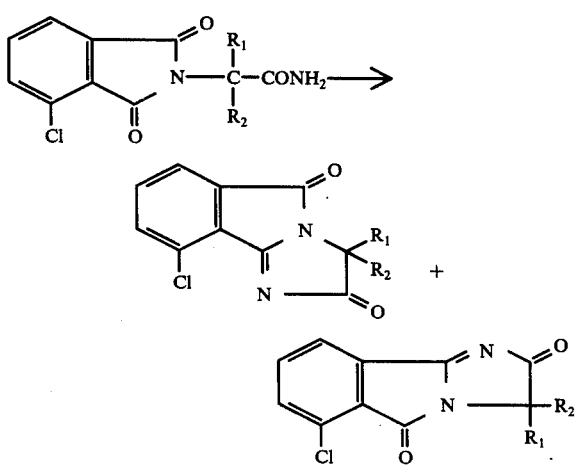

In some cases, as shown in Table I, these are separated either by fractional crystallization or column chromatography. In the other cases, the mixture, indicated by a two-number prefix before the substituent X, is tested for biological activity.

Table I

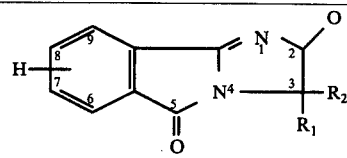

| Catalyst or Base | Solvent | X | $R_1$ | $R_2$ | Melting Point °C |
|---|---|---|---|---|---|
| NaH | Xylene | H | —CH₃ | —CH₃ | 162.5–165 |
| NaH | Xylene | H | —CH₃ | —C₂H₅ | 149–151 |
| NaH | Toluene | H | —CH₃ | —CH₂CH₂CH₃ | 97–98 |
| NaH | Toluene | H | —CH₃ | ▷ | 116–119 |
| NaH | Toluene | H | —CH₃ | —CH(C₂H₅)₂ | 99–101 |
| NaH | Toluene | H | —CH₃ | —CH(CH₃)(C₂H₅) | 85.5–87.5 |
| NaH | Toluene | H | —CH₃ | —C₆H₄Cl | |
| NaH | Toluene | H | —CH₃ | —CH₂C₆H₅ | 153.5–154 |
| NaH | Toluene | H | —C₂H₅ | —C₂H₅ | 112.5–113 |
| NaH | Toluene | H | —CH—CH₂—CH₂—CH₂—CH₂— with CH₃ branch | | 133.5–135 |
| NaH | Toluene | 6/9-CH₃ | —CH₃ | —CH(CH₃)₂ | 139–142 |
| NaH | Toluene | 7/8-CH₃ | —CH₃ | —CH(CH₃)₂ | 99–102 |
| NaH | Toluene | 7/8-Cl | —CH₃ | —CH(CH₃)₂ | 124–127 |
| NaH | Toluene | 6/9-NO₂ | —CH₃ | —CH(CH₃)₂ | 151–183 |
| NaH | Toluene | 7/8-OCH₃ | —CH₃ | —CH(CH₃)₂ | 151.5–153 |
| NaH | Toluene | H | | (CH₂)₅ | 158–162 |
| NaH | Toluene | 6/9-Cl | —CH₃ | —CH(CH₃)₂ | 127.5–129.5 |
| NaH | Toluene | H | —CH₃ | —CH(CH₃)₂ | 98–100.5 |
| NaH | Toluene | 6/9-SCH₃ | | (CH₂)₅ | 263.5–264 |
| NaH | Toluene | 6-Cl | CH₃ | —CH₂CH(CH₃)₂ | 122–124 |
| NaH | Toluene | 9-Cl | —CH₃ | —CH₂CH(CH₃)₂ | 152–154 |
| NaH | Toluene | 6/9-Cl | | (CH₂)₄ | 278–280 |
| NaH | Toluene | H | —CH₃ | —CH₂(CH(CH₃)₂ | 98.5–99 |
| NaH | Toluene | 7/8-CH₃ | | (CH₂)₅ | 183–187 |
| NaH | Toluene | H | | (CH₂)₄ | 185–187 |
| NaH | Toluene | 9-Cl | | (CH₂)₅ | 251–252 |
| NaH | Toluene | 6-Cl | | (CH₂)₅ | 156.5–157.5 |

EXAMPLE 2

Preparation of 3-tert-Butyl-3-methyl-5H-imidazo[2,1-a]-isoindoline-2(3H),5-dione.

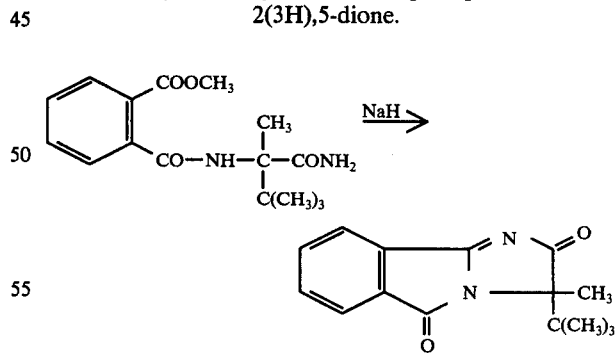

A suspension of sodium hydride (from 1.92 g of a 50% suspension of sodium hydride in mineral oil) in 150 ml toluene is heated under reflux. During 20 minutes is then added portionwise 6.13 g (0.02 mole) methyl N-(1-carbamoyl-1,2,2-trimethylpropyl)phthalamate to the stirred, refluxing, mixture. Heating is continued for 30 minutes after the addition, the mixture filtered through diatomaceous earth, and the solvent removed in vacuo. The residue crystallizes and is recrystallized from a mixture of acetone-hexane to give 3-t-butyl-3-methyl- 3H-imidazo[2,1-a]isoindole-2,5-dione, melting point 136.5°–137.5° C.

The 3,3-diisopropyl-5H-imidazo[2,1-a]isoindole-2(3H),5-dione (melting point 146°–148° C) is prepared in the manner described above, excepting that the methyl ester of N-(1-carbamoyl-1-isopropyl-2-methylpropyl)phthalamic acid is substituted for methyl N-(1-carbamoyl-1,2,2-trimethylpropyl)phthalamate, in the above reaction.

EXAMPLE 3

Four-Step Synthesis for the Preparation of Phthalimidocarboxamide Derivatives Essential for the Preparation of Formula I, Imidazoisoindolediones. Step 1. Preparation of the α-Aminocarbonitrile.

The following is a typical procedure:

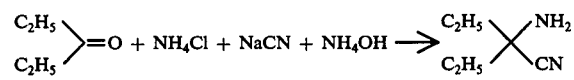

To a mixture containing 79 g (1.477 mole) ammonium chloride and 61.36 g (1.25 mole) sodium cyanide in 400 ml 28% ammonium hydroxide solution is added dropwise with stirring and cooling 86.1 g (1 mole) diethylketone. After stirring overnight, the organic phase is separated and the aqueous phase extracted twice with methylene chloride. The organic phase and extracts are combined, washed with water and dried. The drying agent is removed and the solvent removed in vacuo to leave essentially pure 2-amino-2-ethylbutyronitrile, as shown by the absence of a carbonyl band (1700–1720 cm$^{-1}$) in the infrared spectrum. The aminonitriles can be purified if contaminated with starting ketone by dissolving the crude product in ether, adding anhydrous hydrogen chloride and collecting the precipitated hydrochloride salt. The free aminonitrile can then be regenerated by distributing the salt between methylene chloride and aqueous sodium bicarbonate solution, washing the organic phase with water, drying the organic phase and finally removing the solvent in vacuo.

Using this procedure, the following aminonitriles, reported in Table II below, are prepared as oils and characterized only by their infrared spectra.

TABLE II

Starting Ketone $\underset{R_1}{\overset{R}{\Large>}}=O \rightarrow$ Aminonitrile $\underset{R_1}{\overset{R}{\Large\diagdown}}\hspace{-1em}\underset{CN}{\overset{NH_2}{\Large\diagup}}$

| R | R$_1$ |
|---|---|
| —CH$_3$ | —CH$_3$ |
| —CH$_3$ | —C$_2$H$_5$ |
| —CH$_3$ | —C$_3$H$_7$-n |
| —CH$_3$ | —CH(CH$_3$)$_2$ |
| —CH—CH$_2$—CH$_2$—CH$_2$—CH$_2$— |   |
| \|  CH$_3$ |   |
| —CH$_3$ |   |
| —CH$_3$ | —C(CH$_3$)$_3$ |
| —CH$_3$ | —CH(C$_2$H$_5$)$_2$ |
| —CH$_3$ | —CH(CH$_3$)(C$_2$H$_5$) |
| —CH$_3$ | —CH$_2$C$_6$H$_5$ |
| —C$_2$H$_5$ | —C$_2$H$_5$ |
| —CH(CH$_3$)$_2$ | —CH(CH$_3$)$_2$ |
| —CH$_3$ |   |
|   | ⟨◁⟩ |
|   | —⟨phenyl⟩—Cl |
|   | (CH$_2$)$_5$ |

TABLE II-continued

Starting Ketone $\underset{R_1}{\overset{R}{\Large>}}=O \rightarrow$ Aminonitrile $\underset{R_1}{\overset{R}{\Large\diagdown}}\hspace{-1em}\underset{CN}{\overset{NH_2}{\Large\diagup}}$

| R | R$_1$ |
|---|---|
| (CH$_2$)$_4$ |   |

Step 2. Preparation of the Phthalamic Acids.

The following is a typical procedure:

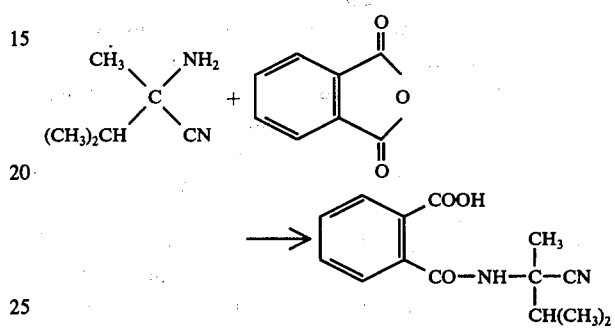

To a stirred boiling mixture of 28.1 g (0.189 mole) of phthalic anhydride in 28 ml methylene chloride is added dropwise 23.6 g (0.21 mole) of 2-amino-2,3-dimethylbutyronitrile in 57 ml methylene chloride. After the addition, heating is continued for 3 hours. The mixture is cooled and the precipitate removed by filtration, washed with methylene chloride and air-dried to give 44.2 g (90%) of N-(1-cyano-1,2-dimethylpropyl)phthalamic acid, melting point 154°–155° C.

Other solvents such as ether, tetrahydrofuran, chloroform, benzene and toluene may be used in place of methylene chloride. The reaction can be run at temperatures from 0°–100° C, but preferably at 20°–50° C.

The phthalamic acids of Table III are prepared by the general method described above using the appropriate phthalic anhydride and appropriate aminonitrile.

TABLE III $$\underset{\substack{\text{COOH} \\ \text{CO—NH—C(R}_1\text{)(R}_2\text{)—CN}}}{\text{benzene ring with X at position 3}}$$

| R$_1$ | R$_2$ | X | Melting Point ° C |
|---|---|---|---|
| —CH$_3$ | —CH$_3$ | H | 135.5–136.5 |
| —CH$_3$ | —C$_2$H$_5$ | H | 138–142 |
| —CH$_3$ | —CH$_2$CH$_2$CH$_3$ | H | 131–131.5 |
| —CH$_3$ | ⟨◁⟩ | H | 138–140 |
| —CH$_3$ | —CH(C$_2$H$_5$)$_2$ | H | 109–113 |
| —CH$_3$ | —CH(C$_2$H$_5$)(CH$_3$) | H | 153.5–154.5 |
| —CH$_3$ | —⟨phenyl⟩—Cl | H | 166–168 |
| —CH$_3$ | —CH$_2$C$_6$H$_5$ | H | 153–154 |
| —C$_2$H$_5$ | —C$_2$H$_5$ | H | 141.5–142.5 |
| —CH(CH$_3$)$_2$ | —CH(CH$_3$)$_2$ | H | 175–176.5 |
| —CH—CH$_2$—CH$_2$—CH$_2$—CH$_2$— \|  CH$_3$ |   | H | 158–162 |

TABLE III-continued

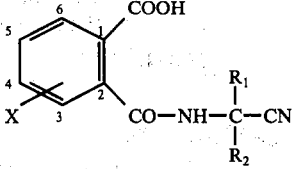

| R₁ | R₂ | X | Melting Point °C |
|---|---|---|---|
| —CH₃ | —CH(CH₃)₂ | 3 and/or 6-CH₃ | 109–112 |
| —CH₃ | —CH(CH₃)₂ | 4 and/or 5-CH₃ | 123–127 |
| —CH₃ | —CH(CH₃)₂ | 4 and/or 5-Cl | 97–100 |
| —CH₃ | —CH(CH₃)₂ | 3 and/or 6-NO₂ | 175–177 |
| —CH₃ | —CH(CH₃)₂ | 4 and/or 5-OCH₃ | 89–92 |

Step 3. Preparation of the Phthalimide Nitriles.

The following is a typical procedure:

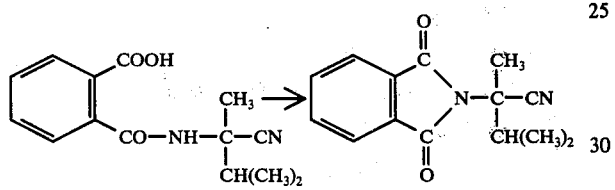

A suspension of 26 g (0.1 mole) of N-(1-cyano-1,2-dimethylpropyl)phthalamic acid in 130 ml methylene chloride is heated with stirring under reflux. Thionyl chloride (8.7 ml, 0.12 mole) is added dropwise, and after the addition, the mixture heated for a further 3 hours. A further 5.8 ml (0.08 mole) thionyl chloride is added and heating continued for a further 2.5 hours. The mixture is cooled down, filtered and the solvent removed in vacuo leaving the product as a pale yellow oil which can be crystallized from etherhexane, melting point 48°–51° C.

Other solvents such as chloroform, benzene, toluene, ethylene dichloride, and the like, can be used in place of methylene chloride. Other reagents such as acetic anhydride and acetyl chloride may be used in place of thionyl chloride, and the temperature employed can vary from about 10°–130° C.

The following Table IV lists the phthalimidocarbonitriles prepared by essentially the above procedure.

TABLE IV

| X | R₁ | R₂ | Melting Point °C |
|---|---|---|---|
| H | —CH₃ | —CH₃ | 113–114.5 |
| H | —CH₃ | —C₂H₅ | oil |
| H | —CH₃ | —CH₂CH₂CH₃ | 64–65.5 |
| H | —CH₃ | ▽ | 57–59 |
| H | —CH₃ | —CH(C₂H₅)₂ | oil |
| H | —CH₃ | —CH(CH₃)(C₂H₅) | oil |

TABLE IV-continued

| X | R₁ | R₂ | Melting Point °C |
|---|---|---|---|
| H | —CH₃ | ⌬—Cl (p-chlorophenyl) | oil |
| H | —CH₃ | —CH₂C₆H₅ | 107.5–109 |
| H | —C₂H₅ | —C₂H₅ | 88.5–89 |
| H | —CH(CH₃)—CH₂—CH₂—CH₂—CH₂— | | 86–87.5 |
| 3-CH₃ | —CH₃ | —CH(CH₃)₂ | 88–92 |
| 4-CH₃ | —CH₃ | —CH(CH₃)₂ | 53–56 |
| 4-Cl | —CH₃ | —CH(CH₃)₂ | 76–79 |
| 3-NO₂ | —CH₃ | —CH(CH₃)₂ | 116–118 |
| 4-OCH₃ | —CH₃ | —CH(CH₃)₂ | 60.5–64 |

Step 4. Preparation of the Phthalimidocarboxamides.

The following is a typical procedure:

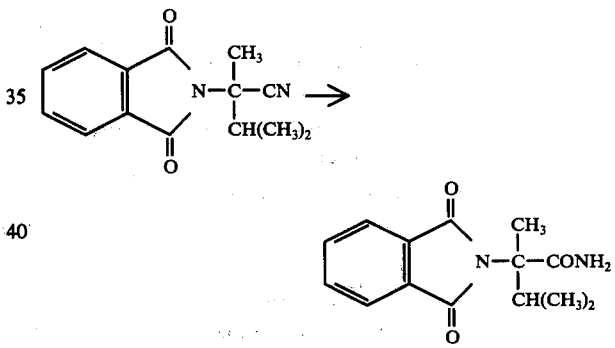

To 404 ml of 85% sulfuric acid is added, with stirring and cooling to maintain a temperature of 14°–16° C, 242.3 g α-isopropyl-α-methyl-1,3-dioxo-2-isoindolineacetonitrile in 67 ml methylene chloride. After the addition (2 hours), the cooling bath is removed and the mixture stirred a further 2 hours at room temperature. The reaction mixture is then poured into a stirred mixture of 2 l water and 300 ml toluene. After 1 hour, the crystalline solid is removed by filtration, washed thoroughly with water, suspended in aqueous sodium bicarbonate solution and again filtered. After washing the solid with water, the product, α-isopropyl-α-methyl-1,3-dioxo-2-isoindolineacetamide, is air-dried and has melting point 165°–166.5° C.

The concentration of the sulfuric acid may be varied from about 70–100%, and the temperature from about 0°–50° C. Co-solvents such as chloroform, ethylenedichloride, may also be used.

The compounds listed in Table V below are prepared using essentially the same method described above.

TABLE V

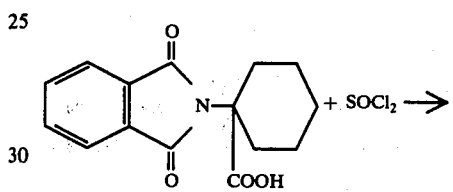

| X | $R_1$ | $R_2$ | Melting Point °C |
|---|---|---|---|
| H | —CH$_3$ | —CH$_3$ | 271-272 |
| H | —CH$_3$ | —C$_2$H$_5$ | 212-215 |
| H | —CH$_3$ | —CH$_2$CH$_2$CH$_3$ | 175-176.5 |
| H | —CH$_3$ | —◁ | 188-189 |
| H | —CH$_3$ | —CH(C$_2$H$_5$)$_2$ | 122.5-124.5 |
| H | —CH$_3$ | —CH(CH$_3$)(C$_2$H$_5$) | 129-135 |
| H | —CH$_3$ | —〈cyclohexyl〉 | 170-173 |
| H | —CH$_3$ | —CH$_2$—C$_6$H$_4$—Cl | |
| H | —CH$_3$ | —CH$_2$C$_6$H$_5$ | 189-190.5 |
| H | —C$_2$H$_5$ | —C$_2$H$_5$ | 189-190 |
| H | —CH—CH$_2$—CH$_2$—CH$_2$—CH$_2$—<br>   \|<br>   CH$_3$ | | 204.5-205.5 |
| 3-CH$_3$ | —CH$_3$ | —CH(CH$_3$)$_2$ | 111-114 |
| 4-CH$_3$ | —CH$_3$ | —CH(CH$_3$)$_2$ | 181-184 |
| 4-Cl | —CH$_3$ | —CH(CH$_3$)$_2$ | 172-174 |
| 3-NO$_2$ | —CH$_3$ | —CH(CH$_3$)$_2$ | 157-159 |
| 4-OCH$_3$ | —CH$_3$ | —CH(CH$_3$)$_2$ | 151-153 |

EXAMPLE 4

Alternate Three-Step Synthesis for the Preparation of Phthalimidocarboxamides Essential for the Preparation of Formula I, Imidazoisoindolediones.

Step 1. Preparation of the Phthalimidocarboxylic Acids.

The following procedure is typical:

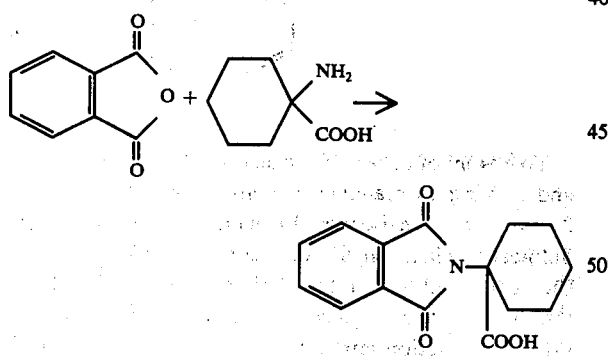

A mixture of 444 g (3 mole) phthalic anhydride, 430 g (3.0 mole) 1-aminocyclohexanecarboxylic acid and 39 ml triethylamine in 4.5 l toluene is heated under reflux with stirring under a Dean-Stark water separator for 21 hours. During this time, 54 ml water is collected. The mixture is slowly cooled to room temperature during which time the product crystallizes from the solution. The product, 1-phthalimidocyclohexanecarboxylic acid, 576.4 g, melting point 176°-178° C, is collected, washed with toluene and air-dried.

Other solvents such as acetic acid, benzene, dimethylformamide, xylenes and the like, as well as direct fusion of the two reactants can be used to effect this reaction at temperatures from about 50°-250° C.

The following compounds listed in Table VI are prepared by essentially the same procedure using the appropriate amino acid and phthalic anhydride.

TABLE VI

| X | $R_1$ | $R_2$ | Melting Point °C |
|---|---|---|---|
| H | —CH$_3$ | —CH(CH$_3$)$_2$ | 159-161 |
| H | —CH$_3$ | —CH$_2$CH(CH$_3$)$_2$ | 133-135 |
| 3-Cl | | (CH$_2$)$_5$ | 193-194 |
| H | —CH$_3$ | —C$_6$H$_5$ | 188-191 |

Step 2. Preparation of the Phthalimidocarbonyl Chlorides.

The following procedure is typical:

A stirred slurry of 300 g (1.1 mole) 1-phthalimidocyclohexanecarboxylic acid in 2.5 l benzene containing 96 ml (157 g, 1.32 mole) thionyl chloride is heated under reflux for 3.25 hours. The solution is then cooled, filtered and the solvent removed in vacuo to leave the 1-phthalimidocyclohexanecarbonyl chloride as an oil, characterized only by its infrared spectrum and used directly for Step 4, described below.

Other solvents such as chloroform, methylene chloride, dichloroethylene, toluene, xylene, and the like, may be used for this reaction at temperatures from about 20°-100° C. Also, other halogenating agents such as thionyl bromide, phosphorus oxychloride may be employed to prepare the reactive acyl halide.

The following compounds, listed in Table VII and characterized only by their infrared spectra, are prepared by essentially the same procedure.

TABLE VII

| X | $R_1$ | $R_2$ |
|---|---|---|
| H | —CH$_3$ | —CH(CH$_3$)$_2$ |
| H | —CH$_3$ | —CH$_2$CH(CH$_3$)$_2$ |
| 3-Cl | | (CH$_2$)$_5$ |

TABLE VII-continued

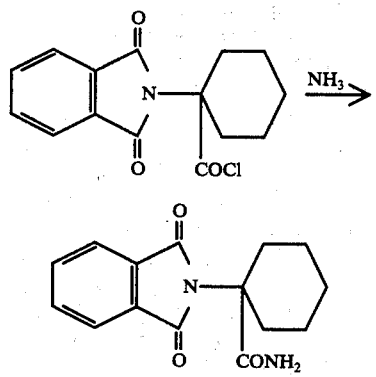

| X | R₁ | R₂ |
|---|-----|------|
| H | —CH₃ | —C₆H₅ |

Step 3. Preparation of the Phthalimidocarboxamides.

The following is a typical procedure:

The crude 1-phthalimidocyclohexanecarbonyl chloride prepared above in Step 3 is dissolved in 3.5 l tetrahydrofuran, and the solution cooled to 5° C. Ammonia is then bubbled into the solution with stirring until infrared analysis of the liquid phase indicates that all the acid chloride is converted to the amide. The reaction mixture is then poured into 8 l of water with stirring, the product removed by filtration, washed with water and air-dried to give 259.1 g of 1-phthalimidocyclohexanecarboxamide, melting point 224°–226° C.

Other solvents such as dioxan, toluene and ether may be used instead of tetrahydrofuran at temperatures preferably between 0°–25° C. When water-immiscible solvents are used, the organic phase must be separated, dried and the solvent removed in vacuo and the product crystallized from an appropriate solvent.

The compounds listed in the following Table VIII are prepared by essentially the same procedure.

TABLE VIII

| X | R₁ | R₂ | Melting Point °C |
|---|-----|------|------|
| H | —CH₃ | —CH(CH₃)₂ | 168–169 |
| H | —CH₃ | —CH₂CH(CH₃)₂ | 170–171 |
| H | (CH₂)₄ |  | 218.5–220 |
| 3-Cl | (CH₂)₅ |  | 193–194 |
| H | —CH₃ | —C₆H₅ | 159–163 |

EXAMPLE 5

Preparation of Phthalamic Acid Esters which are Intermediates for the Preparation of Formula I, Imidazoisoindolediones.

Step 1. Preparation of α-Aminocarboxamides.

The following procedure is typical:

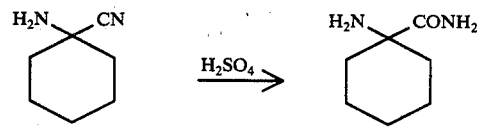

To 20 g concentrated sulfuric acid at 5° C is added with stirring 10 g of 1-aminocyclohexanecarbonitrile. After the addition, the mixture is heated with stirring at 100° C for 1 hour. The hot solution is then poured onto ice, the solution made strongly basic with 50% aqueous sodium hydroxide solution, and extracted three times with chloroform. The extract is washed with water, saturated NaHCO₃ solution, dried, and the solvent removed in vacuo to leave the product, 1-aminocyclohexanecarboxamide, as a crystalline residue, melting point 99°–102° C. This can be recrystallized from either benzene or ether to give a pure product, melting point 101°–102° C.

The α-aminocarboxamides listed in Table IX below were prepared by essentially the procedure described above.

TABLE IX

| R₁ | R₂ | Melting Point °C |
|-----|------|------|
| —CH₃ | —C(CH₃)₃ | 185–186 |
| —CH(CH₃)₂ | —CH(CH₃)₂ | 92–93.5 |
| —CH₃ | —CH₃ | 124.5–125.5 |
| —CH₃ | —CH(CH₃)₂ | 74.5–76 |

Step 2. Preparation of the Phthalamic Acid Esters.

The following is a typical procedure:

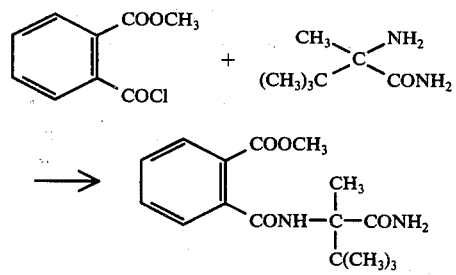

To a stirred suspension of 16.3 g (0.113 mole) of 2-amino-2,3,3-trimethylbutyramide in 226 ml dry tetrahydrofuran containing 16.4 ml dry triethylamine at 5° C is added dropwise a solution containing 22.4 g (0.133 mole) of 2-carbomethoxybenzoyl chloride [Rec. Trav. Chem. 92, 824 (1973)] dissolved in 56 ml dry tetrahydrofuran. After the addition, the mixture is stirred at room temperature for 2 hours and then poured into 400 ml ice cold water. The product was extracted into ethyl acetate, the extract dried over sodium sulfate, the drying agent removed by filtration, and the solvent removed in vacuo. The residual oil crystallizes and the product, methyl N-(1-carbamoyl-1,2,2-trimethylpropyl)phthalamate, recrystallized from acetone-hexane, melting point 146°–147° C.

Other solvents such as ether, dioxane, benzene, toluene, methylene chloride, chloroform, and the like, may be used instead of tetrahydrofuran at temperatures from about 0°–50° C, but preferably at 5°–25° C.

The phthalamic esters listed below in Table X are prepared by essentially the same procedure described above.

TABLE X

| $R_1$ | $R_2$ | Melting Point °C |
|---|---|---|
| —CH(CH$_3$)$_2$ | CH(CH$_3$)$_2$ | 172–173.5 |

EXAMPLE 6

Preparation of (±)-2-Acetylamino-2,3-dimethylbutyric acid.

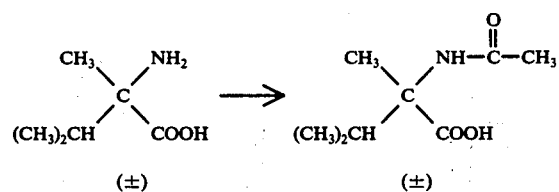

To a stirred solution of 2-amino-2,3-dimethylbutyric acid (13.1 g) in 55 ml 2N NaOH maintained at 5° C is added simultaneously dropwise but separately 17 ml acetic anhydride and 95 ml 2N NaOH so that the pH of the solution is maintained at about 8.5. After stirring at room temperature for a further ½ hour, the mixture is acidified with concentrated HCl and the product, (±)-2-acetylamino-2,3-dimethylbutyric acid, removed by filtration, washed with cold water and air-dried. A sample recrystallized from acetonitrile had melting point 189°–190° C.

EXAMPLE 7

Resolution of 2-Amino-2,3-dimethylbutyric acid.

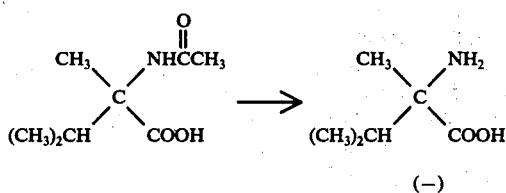

A suspension of 60.6 g (±)-2-acetylamino-2,3-dimethylbutyric acid in 1.5 l water containing 600 mg cobalt acetate tetrahydrate is adjusted to pH 8 by the addition of aqueous lithium hydroxide. The volume of the solution is adjusted to 2.4 l by the addition of water and then 4.0 g of a commercial preparation of hog kidney acylase powder added. The mixture is incubated at 37° C for 24 hours. The pH is again adjusted to 8 with aqueous lithium hydroxide, a further 1 g sample of enzyme added and the incubation continued for a further 4 days.

The digestion is terminated by the addition of 120 ml glacial acetic acid. The mixture is heated to 80° C and 15 g charcoal added. After 1 hour, the mixture is filtered and the filtrate evaporated under reduced pressure to a volume of approximately 1 l and the solution again filtered. The filtrate is evaporated to a volume of approximately 150 ml and cooled in an ice bath. The crystalline precipitate is collected, washed with ice-cold water and air-dried to give 23.6 g of (−)-2-acetylamino-2,3-dimethylbutyric acid, melting point 207°–208° C, $[\alpha]_D^{25}$ −1.33° (MeOH, C 0.06).

The filtrate is concentrated to approximately 100 ml, and approximately 500 ml absolute ethanol added, cooled to 0° C, and after 16 hours the crystalline precipitate of (−)-amino acid removed by filtration, washed with ethanol and air-dried to give 3.7 g of (−)-2-amino-2,3-dimethylbutyric acid.

The filtrate is concentrated to a thick syrup. The syrup in water (100–150 ml) is applied to the top of a column containing 800 ml Dowex 50W-X8 ion exchange resin in its acid form. The column is then eluted with 3 l of water, and the water evaporated under reduced pressure to a small volume, the mixture cooled in an ice bath, the crystalline solid removed by filtration, washed with cold water and air-dried to give 10.3 g of predominantly racemic starting material.

Elution of the column with 4 l of 2N ammonium hydroxide followed by evaporation of the solvent at reduced pressure gives a further 14.95 g of (−)-2-amino-2,3-dimethylbutyric acid. A sample recrystallized from water had $[\alpha]_D^{25}$ −3.6° (H$_2$O, C 0.06).

In order to prepare the (+)-2-amino-2,3-dimethylbutyric acid, 8.65 g of (−)-2-acetylamino-2,3-dimethylbutyric acid is heated under reflux with 240 ml 3N HCl for 15 hours. The mixture is concentrated to dryness, the residue redissolved in 150 ml water and the solution again concentrated to dryness. This is repeated. The residue is then dissolved in a minimum volume of water (approximately 35 ml), cooled in an ice-water bath, and 9.5 ml triethylamine added with swirling followed by 175 ml acetone. The precipitate is removed by filtration, the solid washed successively with 125 ml acetone, 3 × 75 ml chloroform, 100 ml ether and air-dried. This gives 6.45 g (+)-2-amino-2,3-dimethylbutyric acid contaminated by a small amount of its hydrochloride salt but of sufficient purity for the reactions described below. This sequence is summarized below:

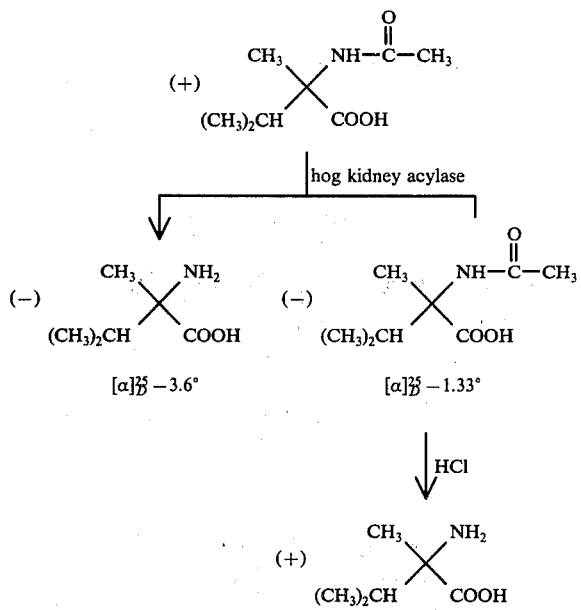

EXAMPLE 8

Preparation of (+)-α-Isopropyl-α-methyl-1,3-dioxo-2-isoindolineacetic acid.

Following the procedure described in Example 4 (Step 1), but substituting (−)-2-amino-2,3-dimethylbutyric acid for 1-aminocyclohexanecarboxylic acid, the product (+)-α-isopropyl-α-methyl-1,3-dioxo-2-isoindolineacetic acid is obtained, melting point 151°–152° C, $[\alpha]_D^{25}$ +10.91° (MeOH, C 0.0976).

EXAMPLE 9

Preparation of (−)-α-Isopropyl-α-methyl-1,3-dioxo-2-isoindolineacetic acid.

Following the procedure described in Example 4 (Step 1), but substituting (+)-2-amino-2,3-dimethylbutyric acid for 1-aminocyclohexanecarboxylic acid, the product (−)-α-isopropyl-α-methyl-1,3-dioxo-2-isoindolineacetic acid is obtained, melting point 151°–153° C, $[\alpha]_D^{25}$ −10.87° (MeOH, C 0.0994).

EXAMPLE 10

Preparation of (−)-α-Isopropyl-α-methyl-1,3-dioxo-2-isoindolineacetamide.

Following the procedure described in Example 4 (Step 2), but substituting (+)-α-isopropyl-α-methyl-1,3-dioxo-2-isoindolineacetic acid for 1-phthalimidocyclohexanecarboxylic acid, the optically active product α-isopropyl-α-methyl-1,3-dioxo-2-isoindolineacetyl chloride is obtained, which is characterized only by its infrared spectrum.

Utilizing directly the above-described acid chloride and following the procedure described in Example 4 (Step 3), but substituting the above-described acid chloride for 1-phthalimidocyclohexanecarbonyl chloride, the product (−)-α-isopropyl-α-methyl-1,3-dioxo-2-isoindolineacetamide is obtained, melting point 118°–119° C, $[\alpha]_D^{25}$ −7.80° (THF, C 0.1013).

EXAMPLE 11

Preparation of
(+)-α-Isopropyl-α-methyl-1,3-dioxo-2-isoindolineacetamide.

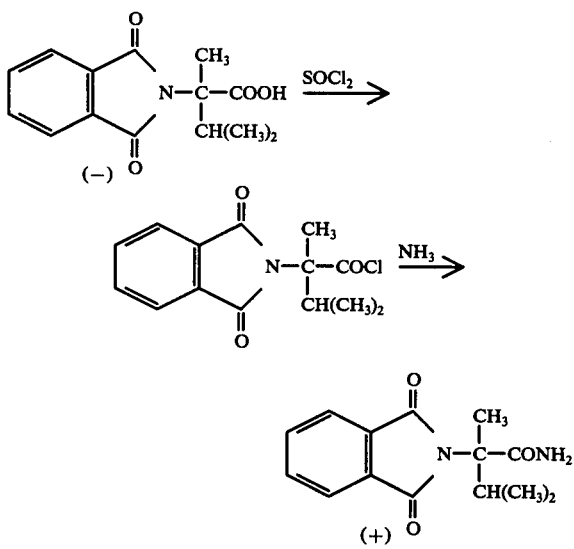

Following the procedure described in Example 4 (Step 2), but substituting (−)-α-isopropyl-α-methyl-1,3-dioxo-2-isoindolineacetic acid for 1-phthalimidocyclohexanecarboxylic acid, the optically active product α-isopropyl-α-methyl-1,3-dioxo-2-isoindolineacetyl chloride is obtained which is characterized only by its infrared spectrum.

Utilizing directly the above-described acid chloride and following the procedure described in Example 4 (Step 3), but substituting the above-described acid chloride for 1-phthalimidocyclohexanecarbonyl chloride, the product (+)-α-isopropyl-α-methyl-1,3-dioxo-2-isoindolineacetamide is obtained, melting point 124°-127° C, $[\alpha]_D^{25}$ +7.19° (THF, C 0.0988).

EXAMPLE 12

Preparation of
(+)-3-Isopropyl-3-methyl-5H-imidazo[2,1-a]-isoindole-2(3H),5-dione.

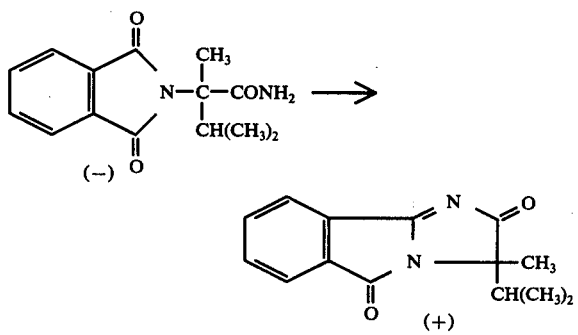

Following the procedure described in Example 1 and sodium hydride as the base, but substituting (−)-α-isopropyl-α-methyl-1,3-dioxo-2-isoindolineacetamide for the racemic compound, the product (+)-3-isopropyl-3-methyl-5H-imidazo-[2,1-a]isoindole-2(3H),5-dione is obtained, melting point 137.5°-139° C, $[\alpha]_D^{25}$ +64.54 (THF, C 0.097).

EXAMPLE 13

Preparation of
(−)-3-Isopropyl-3-methyl-5H-imidazo[2,1-a]-isoindole-2(3H),5-dione.

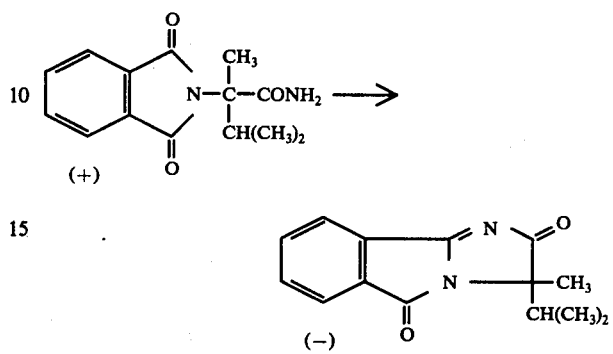

Following the procedure described in Example 1 and sodium hydride as the base, but substituting (+)-α-isopropyl-α-methyl-1,3-dioxo-2-isoindoleacetamide for the racemic compound, the product (−)-3-isopropyl-3-methyl-5H-imidazo[2,1-a]-isoindole-2(3H),5-dione is obtained, melting point 137.5°-139° C, $[\alpha]_D^{25}$ −64.74° (THF, C 0.097).

EXAMPLE 14

The postemergence herbicidal acivity of the compounds of the present invention is demonstrated by the following tests, wherein a variety of monocotyledonous and dicotyledonous plants are treated with test compounds dispersed in aqueous acetone mixtures. In the tests, seedling plants are grown in jiffy flats for about 2 weeks. The test compounds are dispersed in 50/50 acetone/water mixtures containing 0.5% TWEEN®20, a polyoxyethylene sorbitan monolaurate surfactant of Atlas Chemical Industries, in sufficient quantity to provide the equivalent of about 0.14 kg to 11.2 kg per hectare of active compound when applied to the plants through a spray nozzle operating at 40 psi for a predetermined time. After spraying, the plants are placed on greenhouse benches and are cared for in the usual manner, commensurate with conventional greenhouse practices. From 4 to 13 weeks after treatment, the seedling plants, are examined and rated according to the rating system provided below. The data obtained are reported in Table IX below.

| Rating System: | | % Difference in Growth from the Check* |
|---|---|---|
| 0 | No effect | 0 |
| 1 | Possible effect | 1–10 |
| 2 | Slight effect | 11–25 |
| 3 | Moderate effect | 26–40 |
| 5 | Definite injury | 41–60 |
| 6 | Herbicidal effect | 61–75 |
| 7 | Good herbicidal effect | 76–90 |
| 8 | Approaching complete kill | 91–99 |
| 9 | Complete kill | 100 |
| 4 | Abnormal growth, that is, a definite physiological malformation but with an over-all effect less than a 5 on the rating scale. | |

*Based on visual determination of stand, size, vigor, chlorosis, growth malformation and over-all plant appearance.

Plant Abbreviations:
SE - Sesbania (*Sesbania exaltata*)
MU - Mustard (*Brassica kaber*)
PI - Pigweed (*Amaranthus retroflexus*)
RW - Ragweed (*Ambrosia artemisiifolia*)

| Rating System: | % Difference in Growth from the Check* |
| --- | --- |
| MG - Morningglory (*Ipomoea purpurea*) | |
| BA - Barnyardgrass (*Echinochloa crusgalli*) | |
| CR - Crabgrass (*Digitaria sanguinalis*) | |
| FO - Green foxtail (*Setaria viridis*) | |
| WO - Wild oats (*Avena fatua*) | |
| TW - Teaweed (*Sida spinosa*) | |
| VL - Velvetleaf (*Abutilon theophrasti*) | | and cared for in accordance with conventional greenhouse procedures. From 4 to 13 weeks after treatment, the tests are terminated and each cup is examined and rated according to the rating system set forth above. The herbicidal proficiency of the active ingredients of the present invention is evident from the test results which are reported in Table XII below.

TABLE XII

Preemergence Herbicidal Activity

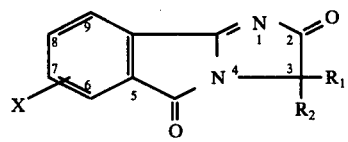

| X | R$_1$ | R$_2$ | Rate kg/hectare | SE | MU | PI | RW | MG | TW | VL | BA | CR | FO | WO |
| --- | --- | --- | --- | --- | --- | --- | --- | --- | --- | --- | --- | --- | --- | --- |
| Cl | (CH$_2$)$_5$ | | 11.2 | — | 4 | 0 | 0 | 4 | 4 | 4 | 4 | 4 | 4 | 4 |
| H | (CH$_2$)$_5$ | | 11.2 | — | 8 | 5 | 1 | 4 | 1 | 2 | 4 | 4 | 4 | 4 |
| H | CH$_3$ | CH(CH$_3$)$_2$ | 11.2 | 8 | 9 | 9 | 9 | 8 | 9 | 9 | 9 | 8 | 9 | 8 |
| | | | 4.5 | 8 | 9 | 9 | 9 | 8 | 9 | 9 | 7 | 7 | 8 | 8 |
| | | | 1.1 | 6 | 8 | 9 | 7 | 7 | 8 | 8 | 9 | 8 | 8 | 4 |
| | | | 0.14 | 0 | 8 | 8 | 4 | 4 | 3 | 4 | 7 | 3 | 5 | 0 |
| CH$_3$ | (CH$_2$)$_5$ | | 11.2 | 0 | 5 | 5 | 0 | 4 | 5 | 4 | 5 | 0 | 0 | 7 |
| Cl | CH$_3$ | CH(CH$_3$)$_2$ | 11.2 | 4 | 9 | 9 | 0 | 5 | 5 | 4 | 4 | 4 | 5 | 4 |
| | | | 4.5 | 0 | 8 | 8 | 1 | 4 | 4 | 7 | 4 | 4 | 1 | — |
| H | CH$_3$ | CH$_3$ | 11.2 | 0 | 8 | 8 | 0 | 5 | 6 | 5 | 7 | 8 | 8 | 4 |
| H | C$_2$H$_5$ | C$_2$H$_5$ | 11.2 | 0 | 7 | 8 | 0 | 4 | 5 | 2 | 0 | 0 | 0 | 0 |
| H | CH$_3$ | C$_2$H$_5$ | 11.2 | 0 | 8 | 8 | 0 | 8 | 8 | 7 | 7 | 7 | 7 | 2 |
| H | CH$_3$ | △ | 11.2 | 0 | 9 | 9 | 0 | 4 | 7 | 7 | 0 | 0 | 5 | 1 |
| 7/8-CH$_3$ | CH$_3$ | CH(CH$_3$)$_2$ | 11.2 | 7 | 9 | 9 | 9 | 8 | 8 | 9 | 9 | 8 | 8 | 8 |
| 6/9-CH$_3$ | CH$_3$ | CH(CH$_3$)$_2$ | 11.2 | 8 | 9 | 9 | | | | | | | | |

TABLE XI

Postemergence Herbicidal Activity

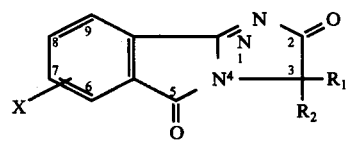

| X | R$_1$ | R$_2$ | Rate kg/hectare | SE | MU | PI | RW | MG | TW | VL | BA | CR | FO | WO |
| --- | --- | --- | --- | --- | --- | --- | --- | --- | --- | --- | --- | --- | --- | --- |
| H | (CH$_2$)$_5$ | | 10.1 | — | 9 | 9 | 3 | 9 | — | 6 | 7 | 9 | 9 | 9 |
| | | | 4.5 | — | 9 | 8 | 0 | 9 | — | 6 | 5 | 3 | 7 | 9 |
| | | | 0.56 | — | 7 | 1 | 4 | 5 | — | 4 | 4 | 2 | 4 | 4 |
| H | CH$_3$ | —CH(CH$_3$)$_2$ | 4.5 | 9 | 9 | 9 | 9 | 9 | 8 | 9 | 8 | 8 | 9 | 9 |
| | | | 1.1 | 9 | 9 | 9 | 9 | 9 | 7 | 9 | 9 | 8 | 8 | 8 |
| | | | 0.28 | 5 | 9 | 9 | 5 | 9 | 7 | 8 | 7 | 6 | 5 | 7 |
| | | | 0.14 | 2 | 9 | 9 | 0 | 4 | 6 | 8 | 4 | 2 | 4 | 4 |
| H | CH$_3$ | △ | 11.1 | 0 | 9 | 9 | 0 | 4 | 7 | 7 | 0 | 0 | 5 | 1 |
| H | CH$_3$ | CH$_3$ | 11.1 | 1 | 6 | 1 | 0 | 0 | 1 | 4 | 7 | 7 | 6 | 4 |
| CH$_3$ | CH$_3$ | —CH(CH$_3$)$_2$ | 11.1 | 6 | 9 | 7 | 4 | 4 | 8 | 9 | 8 | 8 | 6 | 9 |
| 6/9-Cl | CH$_3$ | —CH(CH$_3$)$_2$ | 11.1 | 0 | 8 | 7 | 4 | 4 | 4 | 4 | 0 | 0 | 4 | 4 |

EXAMPLE 15

The preemergence herbicidal activity of the compounds of the present invention is exemplified by the following tests in which the seeds of a variety of monocotyledonous and dicotyledonous plants are separately mixed with potting soil and planted on top of approximately one inch of soil in separate pint cups. After planting, the cups are sprayed with the selected aqueous acetone solution containing test compound in sufficient quantity to provide the equivalent of about 0.14 to 11.2 kg per hectare of test compound per cup. The treated cups are then placed on greenhouse benches, watered

EXAMPLE 16

The effectiveness of the compounds of this invention for the control of undesirable perennial plants, including woody plants, sedges, vines, perennial broadleaf plants and perennial grasses, is demonstrated in the following tests.

In these tests, berry bushes are brought directly from the field and potted, other plants are grown from rhizomes in six-inch pots until the root systems are well established. When the plants are established, the soil in which they are growing is sprayed with a 50/50 aqueous acetone mixture containing sufficient test chemical to provide from about 0.56 to 4.5 kg/hectare thereof.

The treated plants are then placed in the greenhouse and cared for in the usual manner. After 4 weeks, the plants are examined and either rated by the rating system set forth in Example 14, or maintained in the greenhouse and examined and rated at any time up to 13 weeks following treatment. Where woody plants are concerned, 13-week data are reported. Plant species employed in these tests are:

AW — Alligatorweed (*Altermanthera philoxeroides*)
BW — Bindweed (*Convolvulus arvensis L.*)
CT — Canada thistle (*Cirsium arvense L.*)
JG — Johnsongrass (*Sorghum halepense L.*)
QG — Quackgrass (*Agropyron respens L.*)
PN — Purple nutsedge (*Cyperus rotundus L.*)
BB — Blackberry (*Rubus allegheniensis*)
HS — Honeysuckle (*Diervilla lonicera*)
MW — Milkweed (*Asclepias syriaca L.*)
RR — Red raspberry (*Rubus idaeus L.*)
WR — Wild rose (*Rosa multiflora*)

Data are reported in Table XIII below.

TABLE XIII

Preemergence Herbicidal Activity

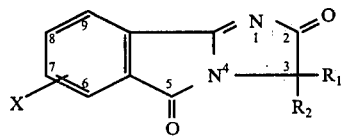

| X | $R_1$ | $R_2$ | Rate kg/hectare | AW | BW | CT | JG | QG | PN | HS | MW | RR | WR | BB |
|---|---|---|---|---|---|---|---|---|---|---|---|---|---|---|
| H | $CH_3$ | $CH(CH_3)_2$ | 4.5 | 9 | 9 | 8 | 7 | 9 | 9 | 9 | 9 | 0 | 7 | 9 |
|   |   |   | 1.1 | 7 | 8 | 5 | 2 | 9 | 8 | 9 | 4 | 0 | 9 | 9 |
|   |   |   | 0.56 | 6 | 3 | 5 | 2 | 8 | 7 | 8 | 4 | 0 | 8 | 0 |

I claim:

1. A method for the control of undesirable plant species comprising applying to the foliage of the undesirable plants or the soil in which they are planted and/or growing, a herbicidally effective amount of a compound having the structure:

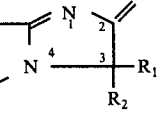

wherein X is H, $CH_3$, $NO_2$, Cl, $OCH_3$ or $SCH_3$; $R_1$ is alkyl $C_1$–$C_4$; $R_2$ is alkyl $C_1$–$C_6$, cycloalkyl $C_3$–$C_6$, alkenyl $C_2$–$C_4$, phenyl, halophenyl or benzyl; and when $R_1$ and $R_2$ are taken together with the carbon to which they are attached, they may form cycloalkyl $C_3$–$C_6$ optionally substituted with methyl; and the optical isomers thereof.

2. A method according to claim 1, wherein the sum of the carbon atoms represented by $R_1$ and $R_2$ is 2 to 4; and the optical isomers thereof.

3. A method according to claim 1, wherein X is hydrogen, methyl or chloro; $R_1$ is alkyl $C_1$–$C_4$; $R_2$ is alkyl $C_1$–$C_3$ or cyclopropyl; and the optical isomers thereof and the compound is applied at the rate of from 0.14 to 11.2 kg per hectare.

4. A method according to claim 1 for controlling perennial plants wherein X is hydrogen, methyl or chloro; $R_1$ is alkyl $C_1$–$C_4$; $R_2$ is alkyl $C_1$–$C_3$ or cyclopropyl and the said compounds are applied at the rate of from 18 to 27 kg/ha.

5. A method according to claim 1 wherein the compound is 3-isopropyl-3-methyl-5H-imidazo[2,1-a]isoindole-2(3H), 5-dione.

6. A method according to claim 1 wherein the compound is 3-isopropyl-7/8-dimethyl-5H-imidazo[2,1-a]isoindole-2(3H),5-dione.

7. A method according to claim 1 wherein the compound is 7/8-chloro-3-isopropyl-3-methyl-5H-imidazo[2,1-a]isoindole-2(3H),5-dione.

8. A method according to claim 1 wherein the compound is 6'/9'-chlorospiro[cyclohexane-1,3'-(3H)]-imidazo[2,1-a]isoindole-2',5'-dione.

9. A method according to claim 1 wherein the compound is 7'/8'-methylspiro[cyclohexane-1,3'-(3H)]-imidazo[2,1-a]isoindole-2',5'-dione.

10. A method according to claim 1 wherein the compound is (+)-3-isopropyl-3-methyl-5H-imidazo[2,1-a]isoindole-2(3H),5-dione.

11. A method according to claim 1 wherein the compound is (−)-3-isopropyl-3-methyl-5H-imidazo[2,1-a]isoindole-2(3H),5-dione.

* * * * *